(12) United States Patent
Vann et al.

(10) Patent No.: US 7,147,764 B2
(45) Date of Patent: Dec. 12, 2006

(54) DUAL ELECTRODE INJECTION OF ANALYTE INTO A CAPILLARY ELECTROPHORETIC DEVICE

(75) Inventors: Charles S. Vann, Burlingame, CA (US); Timothy Z. Liu, Fremont, CA (US)

(73) Assignee: Applera Corporation, Foster City, CA (US)

( * ) Notice: Subject to any disclaimer, the term of this patent is extended or adjusted under 35 U.S.C. 154(b) by 698 days.

(21) Appl. No.: 10/402,173

(22) Filed: Mar. 28, 2003

(65) Prior Publication Data

US 2004/0188253 A1     Sep. 30, 2004

(51) Int. Cl.
 *G01N 27/26*     (2006.01)
(52) U.S. Cl. .................................. 204/604; 204/605
(58) Field of Classification Search ............... 204/604, 204/605
See application file for complete search history.

(56) References Cited

U.S. PATENT DOCUMENTS

| 5,151,164 | A | * | 9/1992 | Blanchard et al. | 204/451 |
|---|---|---|---|---|---|
| 5,344,535 | A | | 9/1994 | Betts et al. | 204/183.1 |
| 5,552,028 | A | | 9/1996 | Madabhushi et al. | 204/451 |
| 5,632,957 | A | | 5/1997 | Heller et al. | 422/68.1 |
| 5,667,654 | A | | 9/1997 | Gombocz et al. | 204/458 |
| 5,800,690 | A | | 9/1998 | Chow et al. | 204/451 |
| 5,869,004 | A | | 2/1999 | Parce et al. | 422/100 |
| 6,001,229 | A | | 12/1999 | Ramsey | 204/451 |
| 6,007,690 | A | | 12/1999 | Nelson et al. | 204/601 |
| 6,013,165 | A | * | 1/2000 | Wiktorowicz et al. | 204/456 |
| 6,086,736 | A | | 7/2000 | Dasgupta et al. | |
| 6,129,826 | A | | 10/2000 | Nikiforov et al. | 204/450 |
| 6,150,119 | A | | 11/2000 | Kopf-Sill et al. | 435/7.1 |
| 6,203,683 | B1 | | 3/2001 | Austin et al. | 204/547 |
| 6,352,838 | B1 | | 3/2002 | Krulevitch et al. | 435/34 |
| 6,537,433 | B1 | | 3/2003 | Bryning et al. | 204/450 |
| 6,811,668 | B1 | * | 11/2004 | Berndt et al. | 204/601 |
| 2003/0116437 | A1 | * | 6/2003 | Burns et al. | 204/453 |

FOREIGN PATENT DOCUMENTS

| DE | 195 00 683 A1 | 6/1996 |
|---|---|---|
| GB | 2 266 153 A | 10/1993 |
| JP | 58-168957 | 5/1983 |
| WO | WO 93/05390 | 3/1993 |
| WO | WO 97/27933 | 8/1997 |
| WO | WO 99/63332 | 12/1999 |
| WO | WO 00/73780 A1 | 12/2000 |
| WO | WO 01/59440 A2 | 8/2001 |
| WO | WO 01/69230 A2 | 9/2001 |
| WO | WO/03/019164 A1 | 3/2003 |
| WO | WO03/023359 A2 | 3/2003 |

OTHER PUBLICATIONS

Ajdari et al. *Free-Flow Electrophoresis With Trapping By A Transverse Inhomogeneous Field*, Proc. Natl. Acad. Sci. USA. vol. 88, pp. 4468-4471 (1991).

Allsopp, et al., *Coupling Of Dielectrophoresis With Capillary Electrophoresis For Microbiological Applications*, Electronic Devices and Circuits Research Projects, http://www.york.ac.us/depts/elec/resrev/sub4/sub412.htm (Dec. 21, 1999).

(Continued)

*Primary Examiner*—Nam Nguyen
*Assistant Examiner*—Anthony Fick
(74) *Attorney, Agent, or Firm*—Kilyk & Bowersox, P.L.L.C.

(57) ABSTRACT

An injection system including a first electrical circuit for concentration of an analyte and a second electrical circuit for injection of the concentrated analyte into an electrophoretic device is described, as well as methods of using the injection system.

16 Claims, 5 Drawing Sheets

OTHER PUBLICATIONS

Asbury et al., *Manipulation Of Single DNA Molecules By Induced-Dipole Forces In Micro-Fabricated Structures*, Dept. of Molecular Biotechnology, University of Washington, Abstract (Feb. 5, 1999).

Asbury et al., *Trapping Of DNA In Nonuniform Oscillating Electric Fields*, Biophysical Journal, vol. 74, pp. 1024-1030 (1998).

Backhouse et al., *DNA Sequencing In A Monolithic Microchannel Device*, Electrophoresis, vol. 21, pp. 150-156, (2000).

Bakewell et al., *Characterisation Of The Dielectrophoretic Movement Of DNA In Micro-Fabricated Structures*, Inst. Phys. Conf. Ser. No. 163, paper presented at the 10th Int. Conf., Cambridge, pp. 73-76 (Mar. 28-31, 1999).

Becker et al., *Polymer Microfabrication Methods for Microfluidic Analytical Applications*, Electrophoresis, vol. 21, pp. 12-26 (2000).

Cheng et al., *Preparation And Hybridization Analysis Of DNA/RNA From E. Coli On Microfabricated Bioelectronic Chips*, Nature Biotechnology 16:541-546 (Jun. 1998).

Chou et al., *DNA Trapping By Electrodeless Dielectrophoresis*, A13.003 Abstract Submitted for the Mar. 2000 Meeting of the American Physical Society (submitted Dec. 3, 1999).

Crippen et al., Dept. of Electrical Engineering, University of Washington, Seattle, Washington, *Examination Of Dielectrophoretic Behavior Of DNA As A Function Of Frequency From 30Hz To 1mhz Using A Flexible Microfluidic Test Apparatus*, Proceedings of the uTAS 2000 Symposium, held in Enshede, The Netherlands (May 14-18, 2000).

Fuhr et al., *Particle Micromanipulator Consisting Of Two Orthogonal Channels With Traveling-Wave Electrode Structures*, Sensor and Actuators, A 41-42:230-239 (1994).

Fuhr et al., *Positioning And Manipulation Of Cells And Microparticles Using Miniaturized Electric Field Traps And Travelling Waves*, Sensors And Materials, Scientific Publishing Division of MY, Tokyo, Japan 7(2):131-146 (1995).

Garcia et al, *The 2D Electric Field Above A Planar Sequence Of Independent Strip Electrodes*, J. Phys. D: Appl. Phys. 33 (2000):1747-1755 (2000).

Goater, A.D. et al., *Single Cryptosporidiumoocyst Isolation And Capture Using A Traveling-Wave Dielectrophoresis Device*, Inst. Phys. Conf. Ser. No. 163, pp. 69-72, paper presented at the 10th Int. Conf., Cambridge (Mar. 28-31, 1999).

Grossman et al., *Capillary Electrophoresis Theory And Practice*, Chapter 1, Academic Press (1992).

Heida et al., *Trapping Neurons By Dielectrophoretic Forces*, Abstract (Jan. 13, 1999), http://www.nmi.de/meameeting/abstracts/heida.htm.

Heller et al., *Control Of Electrohydrodynamic Distortion Of Sample Streams In Continuous Flow Electrophoresis Using Oscillating Fields*, Electrophoresis, 14, 1278-1283 (1993).

Huang et al., *Electric Manipulation Of Bioparticles And Macromolecules On Microfabricated Electrodes*, Anal. Chem. 73(7): 1549-1559 (2001).

Kricka, *Revolution On A Square Centimeter*, Nature Biotechnology 16:513-514 (Jun. 1998).

Lumpkin, *Length Dependent Mobility Of Large DNAs In Oscillating Crossed Electric And Magnetic Fields*, J. Chem. Phys., vol. 92 (6):3848-3852 (Mar. 15, 1990).

Milner et al., *Analysis Of Biological Particles Using Dielectrophoresis And Impedance Measurement*, Biomedical Sciences Instrumentation 34:157-162, (not dated).

Mizuno et al., *Handling Of A Single DNA Molecule Using Electric Field And Laser Beam*, IEEE Transactions on Industry Applications 31(6):1452-1457 (Nov./Dec. 1995).

Morgan et al., *Separation Of Submicron Bioparticles By Dielectrophoresis*, Biophysical Journal 77:516-525 (Jul. 1999).

Morishima et al., *Design Of A Microchannel For Capillary Electrophoresis In Combination With Dielectrophoresis*, Dept. of Chemistry, Stanford University, CA, not dated.

Pethig et al., *Development Of Biofactory-On-A-Chip Technology Using Excimer Laser Micromachining*, J. Micromech. Microeng. 8:57-63 (1998).

Sambrook et al., Molecular Cloning: A Laboratory Manual, Second Edition, Chapter 5, Cold Spring Harbor Laboratory Press (1989).

Simpson et al., *A Transmission Imaging Spectrograph And Microfabricated Channel System For DNA Analysis*, Electrophoresis, vol. 21, pp. 135-149 (2000).

Taylor et al., *Process Control For Optimal PCR Performance In Glass Microstructures*, Journal of Biomedical Microdevices, vol. 1 (1): 65-70 (1998).

Tomlinson et al., *Enhancement Of Concentration Limits Of Detection In CE And CE-MS: A Review Of On-Line Sample Extraction, Cleanup, Analyte Preconcentration, And Microreactor Technology*, J. Cap. Elec., 002:6, pp. 247-266 (1995).

Wang et al., "*Dielectrophoretic Manipulation Of Particles,*" IEEE Transactions On Industry Applications 33(3):660-669 (May/Jun. 1997).

Washizu et al., *Electrostatic Manipulation Of DNA In Microfabricated Structures*, IEEE Transactions of Industry Applications, vol. 26, pp. 1165-1172 (1990).

Washizu et al., *Molecular Dielectrophoresis Of Biopolymers*, IEEE Transactions of Industry Applications, vol. 30, No. 4, pp. 835-843 (1994).

International Search Report from PCT/US02/13721 (Dec. 30, 2002).

International Search Report from co-pending PCT/US01/07576 (May 2, 2002).

International Search Report, mailed Aug. 12, 2004, for International Application No. PCT/US2004/006862 (4 pages).

Hori et al., *Electroconcentration by Using Countercurrent due to Pressurized Flow and Electrophoretic Mobility*, Analytical Chemistry, vol. 65, No. 20, pp. 2882-2886, Oct. 15, 1993.

\* cited by examiner

DUAL ELECTRODE INJECTION OF ANALYTE INTO A CAPILLARY ELECTROPHORETIC DEVICE

FIELD

The present teachings relates to an injection system for use with an electrophoretic device, and methods of using the injection system.

BACKGROUND

Electro-kinetic injection is the most common means of injecting an analyte, for example, DNA fragments, into an electrophoretic device. These devices include analytic devices such as capillary electrophoresis separation analyzers. One problem with electrophoretic devices is that the devices are generally only capable of extracting analyte from a small region or portion of an analyte-containing sample mixture or solution disposed in a sample well. For example, electrophoretic devices are generally capable of extracting only about 0.1 microliter of analyte from 20 microliters of analyte available in an analyte solution. Thus, only about 0.5% of the analyte is used.

SUMMARY

According to various embodiments, a system for injecting an analyte into an electrophoretic device is described. The system can include first and second electric circuits. The system can include three electrodes, for example, such that the first circuit includes a first electrode and a second electrode, and the second circuit includes the first electrode and a third electrode. The first electrode can be a cathode, and the second and third electrode can be anodes. The first circuit can be run at about 5V or less, and can be used to concentrate analyte in an analyte-containing sample solution. The second circuit can be run at about 1000V or more, and can be used to inject the concentrated analyte into a sample injection opening of an electrophoretic device having an electrophoretic channel, wherein the electrophoretic channel has an inner or core diameter, for example, of about 50 microns and an outer diameter of from about 150 microns to about 360 microns.

According to various embodiments, an electrophoretic device is provided that includes such a system for analyte injection.

In other embodiments, a method is provided for injecting an analyte into a sample injection opening of an electrophoretic device. The method can include: providing an analyte-containing mixture in a sample well of the electrophoretic device; concentrating analyte from the mixture in a region of the sample well adjacent an electrode positioned near the sample injection opening; and injecting the concentrated analyte into the sample injection opening. Concentrating the analyte can be effected by operation of a first circuit, and injection of the concentrated analyte can be effected by operation of a second circuit.

Additional embodiments are set forth in part in the description that follows, and in-part will be apparent from the description, or may be learned by practice of the various embodiments described herein.

DETAILED DESCRIPTION OF CERTAIN EMBODIMENTS

Reference will now be made in detail to various embodiments of the present teachings, examples of which are illustrated in the accompanying drawings. While the present teachings are described in conjunction with various certain embodiments, it will be understood that the present teachings are not intended to be limited to those certain embodiments. On the contrary, the present teachings are intended to cover alternatives, modifications, and equivalents, which may be included within the present teachings as defined by the appended claims.

Unless stated otherwise, the following terms and phrases as used herein are intended to have the following meanings.

The term "analyte" refers to a biological substance or chemical compound of interest, or a group or mixture of such substances or compounds. For example, according to various embodiments, an analyte can be a sample of DNA, RNA, PNA, DNA fragments, RNA fragments, PNA fragments, or other biological compounds or fragments thereof. For example, the term "analyte" can refer to a group of different fragments all from the same type of DNA, for example, all from the DNA of a single, individual mammal. In exemplary embodiments, the analyte is capable of undergoing electrophoretic separation. The term "analyte" can herein also refer to two or more substances, compounds, or fragments that can be separated by electrophoresis. An analyte as referred to herein can be a biological substance or compound having either an overall negative charge, an overall positive charge, or a sufficient polarity to be capable of electrophoretic mobility.

The terms "analyte solution," "analyte-containing sample," "analyte-containing sample solution," and variations thereof refer to a mixture or solution comprising one or more analytes and an electrophoresis medium, a carrier medium, a solvent, a vehicle, and/or a diluent for the one or more analytes. The electrophoresis medium, carrier medium, solvent, vehicle, and/or diluent can be, for example, water, an aqueous solution, a buffer solution, a separation medium, or any other material compatible with the analyte(s).

The term "electrophoretic device" refers to any structure or inter-related component parts capable of conducting electrophoresis including the electrophoretic separation of an analyte composed of a collection of fragments. Electrophoretic devices as described herein can include capillary devices and channel devices. Electrophoretic devices can include microfabricated devices, for example, a grooved plate, card, chip, or other substrate. Electrophoretic devices can include an assembly of inter-related component parts, such as a capillary tube, sample well, and detector. The electrophoretic device can include at least one sidewall having an inner surface and an outer surface, wherein the inner surface defines, at least in part, an electrophoretic channel.

The term "electrophoretic channel" refers to an elongate, narrow passage or other structure, for example, a capillary, a microcapillary, a capillary electrophoresis capillary, a tube, or a groove, wherein the electrophoretic channel is capable of containing a volume of analyte solution. The dimensions and shape of the electrophoretic channel can vary. For example, an electrophoretic channel can have a circular, oval, semi-circular, semi-oval, triangular, rectangular, square, or other cross-sectional area, or can have a combination of such cross-sectional areas. The electrophoretic channel can be fabricated by a wide range of technologies, including microfabrication techniques. Exemplary electrophoretic channel structures include a microcapillary, a lumen of an elongated tube, or a groove formed in a chip, wafer or plate. The electrophoretic channel can have a sample injection end having a sample injection opening, and a second end opposite the sample injection end.

The term "sample well" refers to a sample retaining device that is capable of containing, retaining, or otherwise holding an analyte-containing sample solution. According to various embodiments, a sample well can be a discrete structure, such as a vial, test tube, or other sample container, or it can be a recess, hole, or depression formed in, on, or through a substrate. A sample well can be a portion or component of a device that comprises one or more such sample wells, for example, a sample well tray, a microtiter plate, or a channel device. Multiple sample wells, wherein each sample well is a discrete structure, can be used in a device such as a sample well tray or a microtiter plate.

The term "separation medium" refers to a medium in which an electrophoretic separation of one or more sample analytes or components can take place. A separation medium can comprise several components, at least one of which can be a charge-carrying component, or electrolyte. The charge-carrying component can be part of a buffer system for maintaining the separation medium at a defined pH. The separation medium can be, for example, a polymer matrix used for electrophoretic separation.

According to various embodiments, a system for injection of an analyte into an electrophoretic device can include a first circuit and a second circuit. According to various embodiments, the first circuit can include a first electrode and a second electrode, and the second circuit can include the first electrode and a third electrode. At least the first electrode, second electrode, and third electrode can each independently be disposed adjacent an electrophoretic channel of an electrophoretic device. The first electrode can be positioned at or near the sample injection opening of the electrophoretic channel. The injection system can be used to inject an analyte from a sample well containing an analyte solution into an electrophoretic device. One or more analyte in the analyte solution can be concentrated at the second electrode of the injection system by operation of the first circuit at, for example, about 5V or less. The concentrated analyte can be injected into the capillary of the eletrophoretic device by operation of the second circuit at, for example, about 1000V or more, when the electrophoretic channel, for example, a capillary, has an internal diameter of about 100 microns or less, for example, about 50 microns. The capillary can have a cross-sectional area of about 4000 square microns or less, or 2000 square microns, or less. The capillary can have a length of from about 25 cm to about 100 cm, for example, from about 33 cm to about 91 cm.

Figure 1:
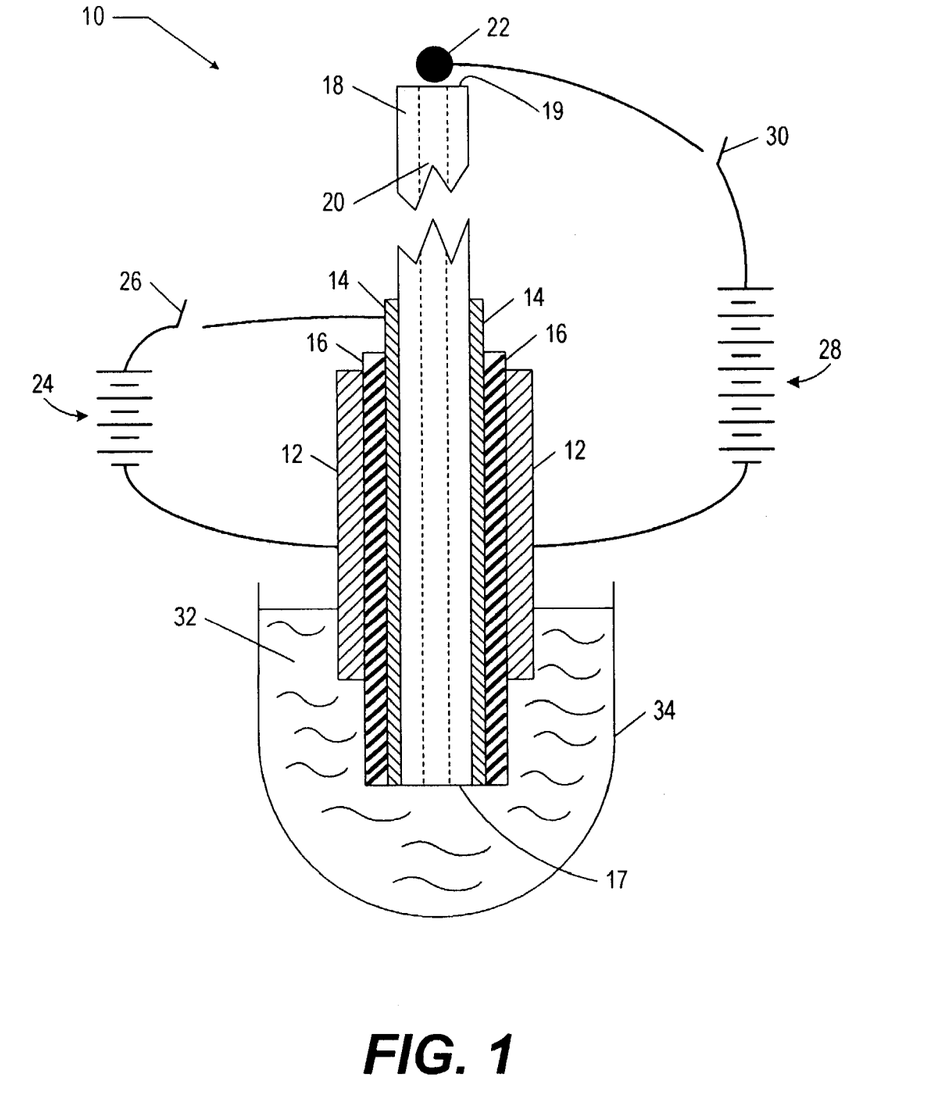
FIG. 1 is a schematic diagram of a dual electrode injection system according to various embodiments.
Figure 2:
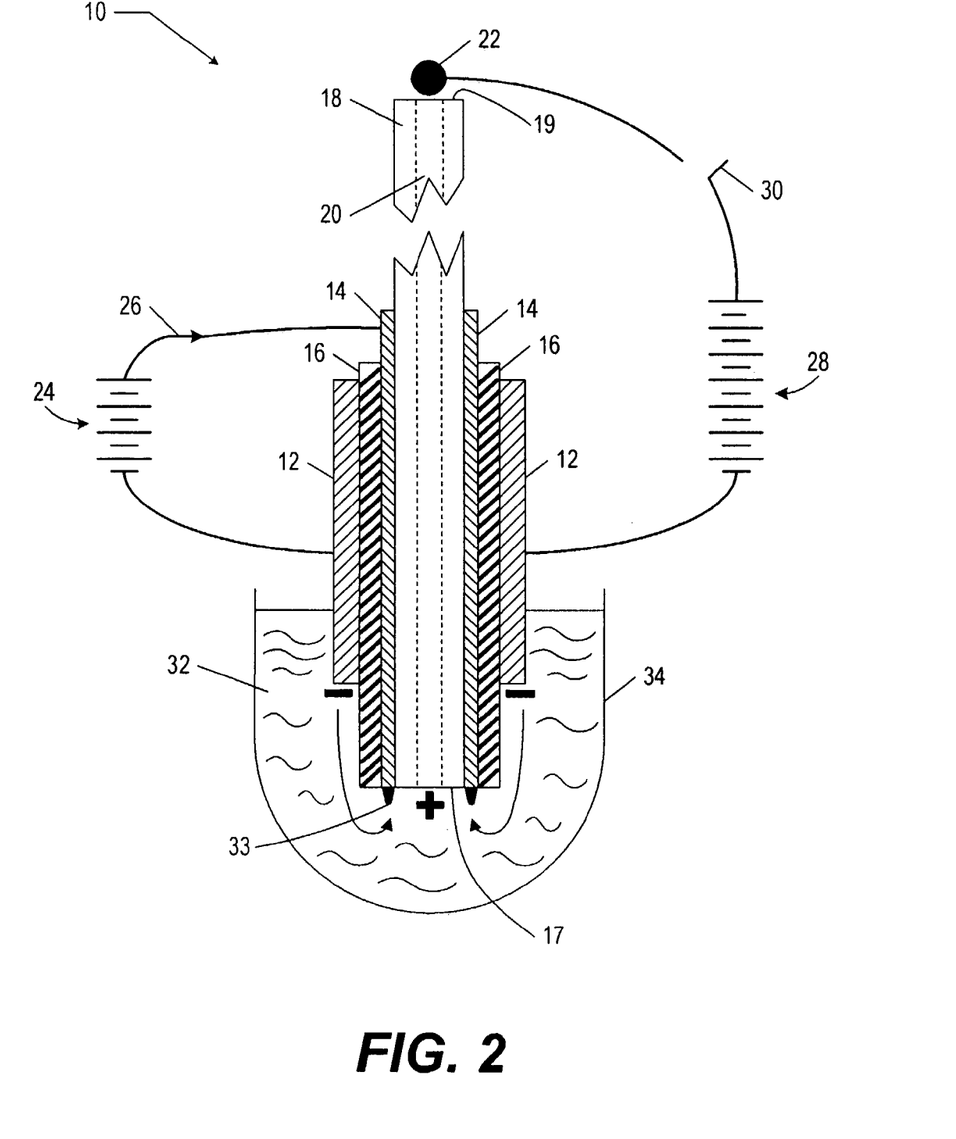
FIG. 2 is a schematic diagram of the dual electrode injection system of FIG. 1 wherein the first circuit is activated.
Figure 3:
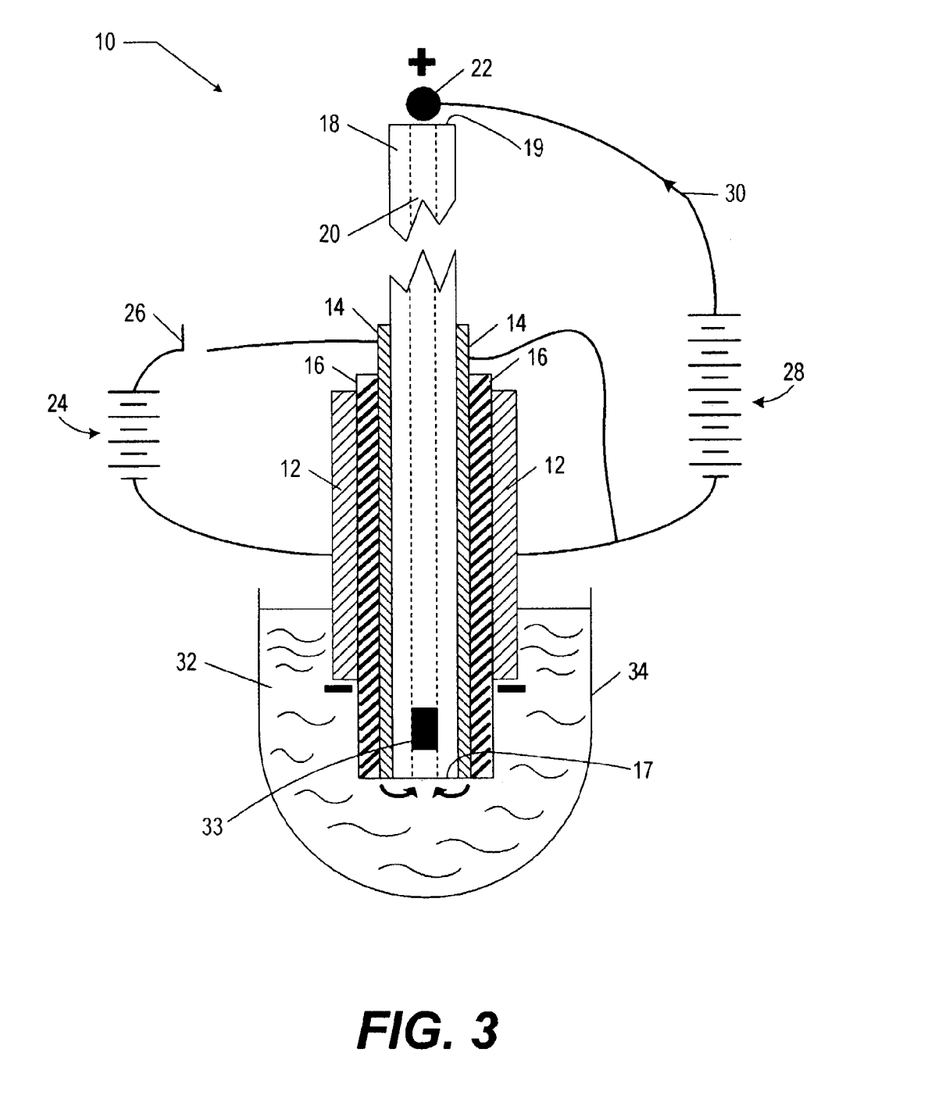
FIG. 3 is a schematic diagram of the dual electrode injection system of FIG. 1 wherein the second circuit is activated.

A detailed description of exemplary embodiments of the system will now be provided with reference to the accompanying figures. As shown in FIGS. 1–5, a system 10 for injecting an analyte into an electrophoretic device includes: a first electrode 12; a second electrode 14 that in combination with the first electrode 12 forms a first circuit 24 having a switch 26; and a third electrode 22 which, in combination with first electrode 12, forms second circuit 28 having a switch 30. As shown in FIGS. 1–3, an insulator 16 can be disposed between the first electrode and the second electrode. The system 10 can be used to form concentrated analyte 33 from analyte solution 32, and inject concentrated analyte 33 into a sample injection opening 20 of an electrophoretic channel, such as capillary 18, of an electrophoretic device or portion thereof.

According to various embodiments and as shown in FIGS. 1–5, the electrophoretic device can include an electrophoretic channel for example, a capillary 18, having a structure capable of retaining an analyte solution. Capillary 18 can include a sample injection opening 20 or starting region at a sample injection end 17. The capillary 18 can be a discrete structure, or can be formed as part of a unitary structure, such as a chip, wafer or plate. The capillary 18 can be filled with a separation medium such as an electrophoresis gel or a polymer matrix useful for conducting electrophoresis.

Figure 4:
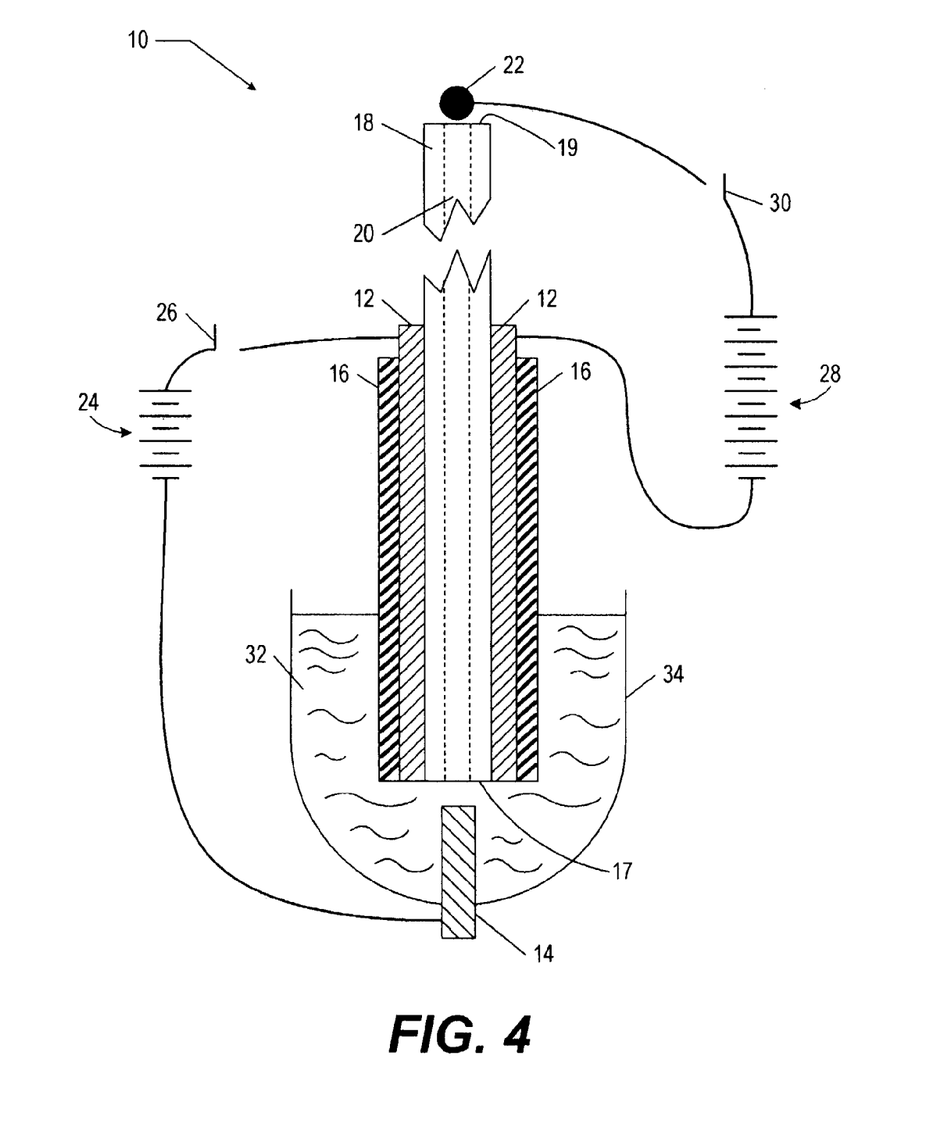
FIG. 4 is a schematic diagram of a dual electrode injection system according to other various embodiments.

According to various embodiments and as shown in FIGS. 1–4, the first electrode 12 can be disposed adjacent the capillary 18. The first electrode 12 can be a cathode. The first electrode 12 can be disposed adjacent one or more sides of the capillary 18, or can surround the capillary 18. The first electrode 12 can be affixed permanently to, or can be detachable from, capillary 18. The first electrode 12 can abut capillary 18. According to various embodiments, first electrode 12 can be separated from capillary 18 by the insulator 16 and the second electrode 14, as shown in FIG. 1. According to various embodiments, the first electrode 12 can be coated on the capillary 18. The first electrode 12 can form a sleeve which can be fitted around capillary 18, as shown in FIG. 4.

The first electrode 12 does not have to extend along the entire length of capillary 18 when the first electrode 12 is disposed adjacent to capillary 18. For example, the first electrode 12 does not necessarily extend to the sample injection end 17 or to the second end 19 of the capillary 18. The first electrode 12 can be disposed spaced a distance from sample injection end 17 of capillary 18 such that the first electrode 12 can be in contact with an analyte solution when the sample injection end 17 of capillary 18 is placed in contact with the analyte solution.

Figure 5:
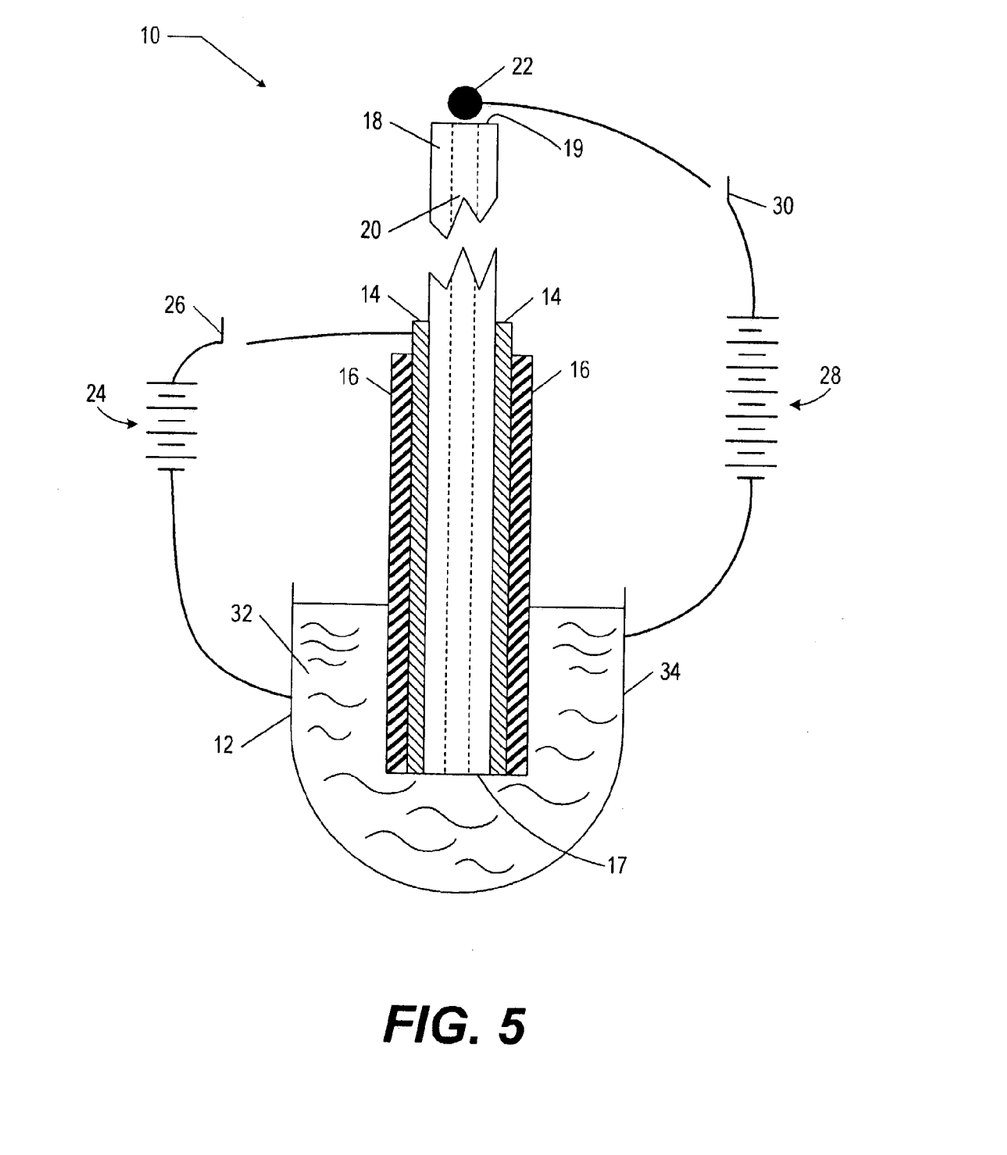
FIG. 5 is a schematic diagram of a dual electrode injection system according to various embodiments wherein a sample well functions as a cathode.

According to various other embodiments and as shown in FIG. 5, the first electrode 12 can be in the form of a sample well 34. When the first electrode 12 is a sample well 34, the sample well can be formed of a conductive material. When the first electrode 12 is a sample well, the sample well can be a discrete structure, or can be a portion of a device comprising one or more sample wells, such as a sample well tray, a microtiter plate, or a channel device. According to various embodiments, the first electrode 12 can be a material coated onto an interior sidewall of the sample well.

According to various embodiments, the first electrode can be formed of any electrically conductive material, for example, platinum, stainless steel, copper, silver, gold, or alloys thereof. Other suitable electrically conductive materials for use as an electrode are known to those of ordinary skill in the art. The first electrode 12 can be a cathode.

According to various embodiments, a second electrode 14 can be disposed adjacent the sample injection opening 20 at the sample injection end 17 of the capillary 18. As shown in FIGS. 1–3 and 5, the second electrode 14 can be disposed immediately adjacent the capillary 18. When disposed immediately adjacent the capillary 18, the second electrode 14 can be located along one or more sides of capillary 18, or can completely surround the capillary 18. When disposed immediately adjacent the capillary 18, the second electrode 14 can be affixed permanently to, or can be detachable from, the capillary 18. The second electrode 14 can be coated on the capillary 18. The second electrode 14 can be formed as a sleeve which can be fitted around capillary 18. According to various embodiments, the second electrode 14 can extend from the sample injection end 17 of capillary 18 along a length of capillary 18, but does not necessarily extend to the second end 19 of capillary 18. The second electrode can have a diameter of, for example, about 700 microns, although other diameters can be used as appropriate, and can be determined by those of ordinary skill in the art. According to various embodiments, the second electrode 14 can be formed of any suitable electrically conductive material, such as, for example, platinum, stainless steel, copper, silver, gold, or alloys thereof. Other suitable electrically conductive materials known to those of ordinary skill in the art can also be used. According to various embodiments, the second electrode 14 can be an anode.

According to various embodiments, and as shown in FIG. 4, the second electrode 14 can be located in sample well 34 such that one end of the second electrode 14 is located near the sample injection opening 20 at the sample injection end 17 of capillary 18. The second electrode 14 can be permanently affixed to, or removable from, sample well 34. The second electrode 14 can be set in sample well 34, or can extend through sample well 34. In embodiments where the second electrode 14 is set in or extends through sample well 34, the second electrode 14 can be placed close to the sample injection opening 20 of the sample injection end 17 of capillary 18. For example, the second electrode 14 can be positioned in sample well 34 such that second electrode 14 is about 100 microns or less from the sample injection end 17 of capillary 18. According to various embodiments, second electrode 14 can be positioned in sample well 34 such that second electrode 14 is about 75 microns or less from the sample injection end 17 of capillary 18.

According to various embodiments, the first electrode 12 and the second electrode 14 can both be disposed adjacent the capillary tube 18, as shown in FIGS. 1–3. When the first electrode 12 and the second electrode 14 are both disposed adjacent to, or both surround, capillary 18, the first electrode 12 and second electrode 14 can be separated by an insulator 16 such that the second electrode 14 is immediately adjacent the capillary 18, and the insulator 16 is disposed between the second electrode 14 and the first electrode 12. In an exemplary embodiment, the insulator 16 can cover the entire length of a second electrode 14. The insulator 16 can leave uncovered the end of the second electrode 14 located near the sample injection opening 20 at the sample injection end 17 of capillary 18. The insulator 16 can leave only a tip of the second electrode 14 exposed where concentrated analyte 33 is formed by the system 10 during operation.

According to various embodiments and as shown in FIGS. 1–5, the third electrode 22 can be disposed adjacent capillary tube 18 at the second end 19 of capillary tube 18, that is, opposite the sample injection end 17. The third electrode 22 can be permanently or removably attached to the capillary tube 18. According to various embodiments, the third electrode 22 can be any suitable electrically conductive material, such as, for example, platinum, stainless steel, copper, silver, gold, or alloys thereof. Other suitable electrically conductive materials are known to those of ordinary skill in the art. The third electrode 22 can be an anode.

According to various embodiments and as shown in FIGS. 1–5, the first electrode 12 and the second electrode 14 can form a first circuit 24 through an analyte solution 32. The first circuit 24 can have a switch 26 to control the flow of power from a power source, such as a battery, to the first circuit 24. The first circuit 24 can be formed such that when no power is provided to the first circuit 24, the first electrode 12 and the second electrode 14 are supplied with no voltage by the first circuit. When power is provided to the first circuit 24 by closing the switch 26, the first electrode 12 can be negatively charged, making the first electrode 12 a cathode, and the second electrode 14 can be positively charged, making the second electrode 14 an anode. Operation of the first circuit can be used to concentrate one or more analytes from the analyte solution 32 at the second electrode 14, as shown in FIG. 2. Concentrated analyte 33 can be formed adjacent, for example, the second electrode 14, the sample injection opening 20, and the sample injection end 17, as shown in FIG. 2.

The first electrode and the second electrode can be separated by any distance suitable to create an electric field gradient sufficient to move an analyte through the analyte solution towards the sample injection opening of the electrophoretic channel, such as a capillary, to form concentrated analyte suitable for injection into the electrophoretic channel. For example, the distance between the first electrode and the second electrode can be about 500 microns, when the electrophoretic channel is a microcapillary. Other suitable distances as known to those skilled in the art can be used based on factors including the respective locations of the first electrode and the second electrode, the size of the sample well, the diameter of the electrophoretic channel, and the composition and amount of the analyte solution.

According to various embodiments, first circuit 24 can be powered by a power supply sufficient to apply a voltage differential of about 5V or less, about 4V or less, about 3.5V or less, about 3V or less, or about 1V or more, between the first electrode 12 and the second electrode 14. Maintaining a low voltage in the first circuit 24 can reduce or eliminate the formation of bubbles during concentration of an analyte from the analyte solution at or near the second electrode 14. For example, at 3.5V or less, few or no bubbles are formed by electrolysis caused by the first circuit. The voltage differential applied between the first electrode 12 and the second electrode 14 of the first circuit 24 can be greater than 5V, depending on the properties of the analyte and the injection system. An appropriate voltage can be determined by those of ordinary skill in the art based on the analyte, analyte solution, electrophoretic device, and speed of analyte concentration desired.

According to various embodiments, the power supply for the first circuit 24 can supply direct current (DC) to the electrodes. According to various other embodiments, the power supply can supply alternating current (AC) and can be used in conjunction with a converter, such as a rectifier and/or capacitor, to convert AC to DC such that direct current can be provided to the electrodes.

According to various embodiments, the first circuit 24 can be operated for a period of time sufficient to concentrate an analyte at or near the second electrode 14. The first circuit 24 can be operated for a period of about 30 seconds or less, for example, about 25 seconds or less, about 20 seconds or less, or about 15 seconds or less. Other periods of time can be used as appropriate for a given combination of analyte, analyte solution, electrophoretic device, voltage, and desired speed of analyte concentration or concentration time before injection.

According to various embodiments, the first electrode 12 and the third electrode 22 can form a second circuit 28 through a separation medium, for example, a polymer matrix, in the sample injection opening 20 of the capillary 18. The separation medium can be any polymer, gel, or composition suitable for electrolytic separation of one or more analytes sought to be electrophoresed. The separation medium in the capillary 18 can be the same as one or more components of the analyte solution, such as the electrophoresis medium or the carrier medium, or can be different than the components of the analyte solution. The second circuit 28 can have a switch 30 to control the flow of power from a power source to the second circuit 28. The second circuit 28 can be formed such that when no power is provided to the second circuit, the first electrode 12 and the third electrode 22 have no voltage provided thereto by the second circuit. When power is provided to the second circuit 28 by closing the switch 30, the first electrode 12 is negatively charged, making the first electrode 12 a cathode, and the third electrode 22 is positively charged, making the third electrode 22 an anode. When the second circuit 28 is operated, the power supplies can be operated such that no power is provided to the second electrode 14 from the second circuit 28. The second electrode 14 can be located within the region of the electric field generated by the first electrode 12.

The first electrode 12, the second electrode 14, and the third electrode 22 can all be part of the second circuit 28, wherein the first electrode 12 and the second electrode 14 can both function as cathodes, and the third electrode 22 can function as an anode. As shown in FIG. 3, operation of the second circuit can effect injection of the concentrated analyte 33 into the capillary 18 by repelling the concentrated analyte 33 from the first electrode 12 in the analyte solution 32, and attracting the concentrated analyte 33 toward the third electrode 22 at the second end 19 of the capillary 18.

The first electrode and the third electrode can be separated by any distance suitable to create an electric field gradient sufficient to inject concentrated analyte through the sample injection opening into the electrophoretic channel, for example, into a microcapillary. A suitable distance can be determined by those skilled in the art based on various factors such as the diameter and length of the electrophoretic channel, the separation medium, the charge of the concentrated analyte, and the power applied to the second circuit. For example, the first electrode and the third electrode can be separated by a distance of from about 31 cm to about 91 cm when the electrophoretic channel is a microcapillary.

According to various embodiments, the second circuit 28 can be powered sufficiently to apply a voltage of about 1000V or more, for example, about 1500V or more, between the first electrode 12 and the third electrode 22, and optionally between the first and second electrodes and the third electrode if the second electrode 14 is part of the second circuit 28. The voltage applied to the second circuit 28 can be sufficient to repel concentrated analyte 33 from where the concentrated analyte 33 is collected at or near the second electrode 14. The voltage supplied to the second circuit 28 can be sufficient to draw or attract the concentrated analyte 33 towards the third electrode 22 through the capillary 18.

According to various embodiments, the power supply for second circuit 28 can supply direct current (DC) to the electrodes. According to various other embodiments, the power supply can supply alternating current (AC) and can be used in conjunction with a converter, such as a rectifier and/or capacitor, to convert AC to DC such that direct current can be provided to the electrodes.

According to various embodiments, the second circuit 28 can be run at a voltage of about 1000V or more, for example, about 1500V or more, for a period of time sufficient to inject concentrated analyte 33 into the capillary 18. According to various embodiments, the second circuit 28 can be run for a period of at least about 15 seconds, for example, at least about 20 seconds, at least about 25 seconds, or at least about 30 seconds, after which time the voltage can be continued, increased, decreased, or discontinued. Other periods of time can be used as appropriate for a given combination of analyte, analyte solution, electrophoretic device, voltage, and desired speed of separation of the analyte(s). For example, according to various embodiments, the second circuit 28 can be operated at an initial voltage of about 1500V for a period of about 20 seconds to inject the concentrated analyte 33 into the capillary 18, and then the voltage can be increased to about 15 KV for a period sufficient to effect electrophoretic separation of the analyte(s) from other components and/or analytes in the analyte solution.

In operation, injection system 10 can be placed in fluid communication with a sample well 34 containing an analyte solution 32. The electrophoretic channel, for example, capillary 18, can be placed in fluid communication with the analyte solution 32 in the sample well 34. The capillary 18 can be separated from sample well 34 and subsequently placed or caused to be in fluid communication therewith, or the capillary 18 can be permanently connected to the sample well 34, such as by a unitary construction of a microfluidic device as, for example, in a card, chip, or plate device. According to various method embodiments, the first electrode 12 can be disposed adjacent the capillary 18, and at least a portion of the first electrode 12 can be placed in contact with the analyte solution 32. According to various other method embodiments, the first electrode 12 can be in the form of sample well 34, and the first electrode 12 can be filled with an analyte solution 32 into which the capillary 18 can be placed. The method can utilize a device wherein the second electrode 14 can be disposed adjacent the sample injection end 17 of the capillary 18, and at least a portion of the second electrode 14 can be in contact with the analyte solution 32. The method can utilize a device wherein the second electrode 14 can be in contact with the capillary 18, as shown in FIGS. 1–3 and 5, or the second electrode 14 can be located in the sample well 34, as shown in FIG. 4.

According to various embodiments, the injection system 10 can be in fluid communication with the analyte solution 32. The switch 26 can be closed, providing power to the first circuit 24 such that the first electrode 12 can be negatively charged and the second electrode 14 can be positively charged. The switch 26 can be maintained in the closed position for a period of time sufficient to concentrate analyte from the analyte solution 32 at or near the second electrode 14. For example, the switch 26 can be maintained in the closed position for a period of about 30 seconds or less, for example, about 25 seconds or less, about 20 seconds or less, or about 15 seconds or less. While switch 26 is closed, switch 30 can remain open.

After analyte is concentrated at the second electrode 14, the switch 26 can be opened so that no power is provided to the first circuit 24. The switch 30 can then be closed to provide power to the second circuit 28. When the second circuit 28 is powered, the first electrode 12 can be negatively charged and the third electrode 22 can be positively charged, and, optionally, the second electrode 14 can be negatively charged. The switch 30 can be maintained in the closed position for a period of time sufficient to draw at least a portion of the concentrated analyte 33 from the second electrode 14 through the sample injection opening 20 of the capillary 18 and toward the third electrode 22. For example, switch 30 can be maintained in the closed position for a period of about 15 seconds or more, for example, about 20 seconds or more, about 25 seconds or more, or about 30 seconds or more. While the switch 30 is closed, the switch 26 can remain open.

According to various embodiments, changing the charge of the second electrode 14 from a positive charge to either no charge or to a negative charge aids in releasing concentrated analyte 33 from at or near the second electrode 14. When the charge of the second electrode 14 is changed from a positive charge to a negative charge, the concentrated analyte 33 can be actively repulsed from the second electrode 14.

According to various embodiments, the use of the injection system 10 can result in the collection of all analyte(s) from the analyte solution 32 disposed in the sample well 34. The efficiency of analyte concentration and injection using the injection system 10 enables the use of much smaller analyte concentrations in analyte solution 32 relative to concentrations that can be used in other known analyte collection techniques wherein analyte is collected from only a small portion of analyte solution in a sample well. The injection system 10 can provide a concentration of at least about 70%, for example, at least about 80%, at least about 90%, at least about 95%, or at least about 99% of the analyte in the sample well, in a region at, near, or around the second electrode 14, and near the sample injection opening 20 of the capillary 18. According to various embodiments, injection system 10 can provide the injection of at least about 70%, for example, at least about 80%, at least about 90%, at least about 95%, or at least about 99% of the available analyte in the analyte solution into the sample injection opening 20 of the capillary 18. According to various embodiments, the injection system 10 can inject about 99% of the available analyte from the analyte solution from the sample well 34 into the capillary 18. The ability to use a lower concentration of analyte in a sample, due to the use of the injection system 10, enables conservation of samples for other analyses or processing, and can reduce or eliminate a need for sample amplification, such as, for example, DNA amplification by polymerase chain reaction (PCR).

Injection of analyte into an electrophoretic device using an injection system 10 according to various embodiments can be carried out as follows:

a) add an analyte solution 32 to a sample well 34;
b) place injection system 10 in fluid communication with the analyte solution 32 in the sample well 34;
c) close the switch 26 for a first electrical circuit 24 to provide a charge to a first electrode 12 and an opposite charge to a second electrode 14; and
d) open the switch 26 and close a switch 30 for a second electrical circuit 28 to provide a first charge to the first electrode 12, an opposite charge to a third electrode 22, and, optionally, the same charge as the first charge to the second electrode 14.

According to various embodiments, the step of closing the switch 26 can occur for a period of time sufficient to concentrate analyte at or near the second electrode 14. According to various embodiments, the switch 30 can be closed for a period of time sufficient to inject concentrated analyte 33 from the second electrode 14 into the sample injection opening 20 of the capillary 18.

According to various embodiments, the charges to, attraction of, and repulsion of analyte resulting from the electrodes of the system 10 do not damage sensitive biological components or agents from the analyte solution, such as fluorophores.

According to various embodiments, a method of using a system for the injection of an analyte into an electrophoretic device is described. The method can include adding an analyte solution to a sample well, concentrating analyte in the sample well at or near an electrode positioned near a sample injection opening of an electrophoretic device, and injecting or directing the analyte into the sample injection opening of the electrophoretic device. According to various embodiments, concentrating the analyte can be effected by operation of a first circuit, and injection of the analyte can be effected by operation of a second circuit.

As described herein, an analyte is injected into a capillary of an electrophoretic device. The system and method described herein exemplify an analyte of negative charge. However, the system as described can be modified for use with positively charged analytes by reversing the respective charges on the respective first, second, and third electrodes.

Other embodiments will be apparent to those skilled in the art from consideration of the present specification and practice of the present teachings disclosed herein. It is intended that the present specification and examples be considered as exemplary only.

What is claimed is:

1. A system for injecting an analyte, comprising:
   a first electrical circuit including a first electrode, a second electrode, and an interruptible electrical communication between the first electrode and the second electrode;
   a second electrical circuit including the first electrode, a third electrode, and an interruptible electrical communication between the first electrode and the third electrode; and
   an electrophoretic device including an electrophoretic channel, the electrophoretic channel including a sample injection end having a sample injection opening, and a second end opposite the sample injection end, wherein the second electrode is disposed along and outside the electrophoretic channel and the electrophoretic device includes at least one sidewall having an inner surface and an outer surface, the electrophoretic channel is defined at least in part by the inner surface, and the system further includes an insulator, and wherein the second electrode is disposed between the outer surface and the insulator, and the insulator is disposed between the second electrode and the first electrode, and wherein
   the first electrode is disposed adjacent and outside the electrophoretic channel, the second electrode is disposed adjacent the sample injection opening, and the third electrode is disposed adjacent the second end of the electrophoretic channel.

2. The system of claim 1, further including a sample well, and an analyte solution disposed in the sample well, wherein the analyte solution is in fluid communication with the sample injection opening.

3. The system of claim 2, wherein the sample well is permanently positioned relative to the electrophoretic channel.

4. The system of claim 1, wherein the first circuit is capable of applying a negative voltage to the first electrode.

5. The system of claim 1, wherein the first circuit is capable of applying a positive voltage to the second electrode.

6. The system of claim 1, wherein the first circuit is capable of applying a voltage differential of about =5V or less between the first electrode and the second electrode.

7. The system of claim 1, wherein the first circuit is capable of applying a voltage differential of about 3V or less between the first electrode and the second electrode.

8. The system of claim 1, wherein the second circuit is capable of providing a negative charge to the first electrode.

9. The system of claim 1, wherein the second circuit is capable of providing a positive charge to the third electrode.

10. The system of claim 1, wherein the second circuit further includes an electrical communication between the second electrode and the third electrode.

11. The system of claim 10, wherein the second circuit is capable of providing a negative charge to the second electrode.

12. The system of claim 1, wherein the second circuit is capable of providing a voltage differential of about 1000V or more between the first electrode and the third electrode.

13. The system of claim 1, wherein the first electrode includes a structure capable of containing an analyte solution.

14. The system of claim 13, wherein the first electrode is a sample well.

15. The system of claim 13, wherein the first electrode comprises a coating on an interior surface of a sample well.

16. The system of claim 1, wherein the electrophoretic channel contains an electrophoretic separation medium.

* * * * *